United States Patent [19]
Archibald et al.

[11] 4,073,790
[45] Feb. 14, 1978

[54] PIPERIDINO UREAS AND THIOUREAS

[75] Inventors: John Leheup Archibald, Windsor; John Lambert Jackson, Exmouth, both of England

[73] Assignee: John Wyeth & Brother Limited, Maidenhead, England

[21] Appl. No.: 549,271

[22] Filed: Feb. 12, 1975

[30] Foreign Application Priority Data

Feb. 18, 1974 United Kingdom ............... 7278/74

[51] Int. Cl.$^2$ ........................................... C07D 211/58
[52] U.S. Cl. ........................... 260/293.73; 260/293.76; 260/293.77; 424/267; 260/293.67; 260/293.68; 260/293.69
[58] Field of Search ...................... 260/293.73, 293.76, 260/293.77

[56] References Cited

FOREIGN PATENT DOCUMENTS 1,345,872 2/1974 United Kingdom ............ 260/293.78

Primary Examiner—Norma S. Milestone

[57] ABSTRACT

This invention relates to compounds having the formula:

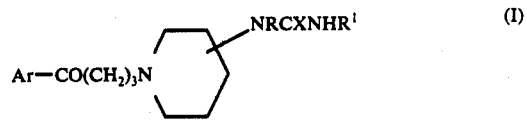

and acid addition and quaternary ammonium salts thereof, wherein R represents hydrogen or lower alkyl, R$^1$ represents hydrogen, lower alkyl, cycloalkyl of 5 to 7 carbon atoms, substituted or unsubstituted aralkyl of 7 to 12 carbon atoms, substituted or unsubstituted aryl (including heterocyclic aryl), or substituted or unsubstituted aroyl, Ar represents a substituted or unsubstituted phenyl radical and X represents oxygen or sulphur, which exhibit action on the cardiovascular system.

15 Claims, No Drawings

PIPERIDINO UREAS AND THIOUREAS

The invention relates to novel piperidine derivatives, to processes for preparing them and to pharmaceutical compositions containing them.

The present invention provides compounds of the general formula:

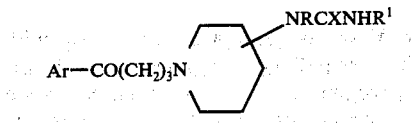   (I)

and acid addition and quaternary ammonium salts thereof, wherein R represents hydrogen or lower alkyl, $R^1$ represents hydrogen, lower alkyl, cycloalkyl of 5 to 7 carbon atoms, substituted or unsubstituted aralkyl of 7 to 12 carbon atoms, substituted or unsubstituted aryl (including heterocyclic aryl), or unsubstituted or unsubstituted aroyl, Ar represents a substituted or unsubstituted phenyl radical and X represents oxygen or sulphur.

The phenyl radical Ar may be substituted by halogen, e.g., fluorine or chlorine, lower alkoxy, e.g., methoxy, aryl lower alkoxy, e.g., benzyloxy, hydroxy, lower alkyl e.g., methyl, alkylenedioxy, e.g., methylenedioxy, or trihalo lower alkyl, e.g., trifluoromethyl.

The term "lower" in relation to alkyl and alkoxy radicals used herein means that the radical contains from 1 to 6 carbon atoms. Usually such radicals containing from 1 to 4 carbon atoms are preferred.

Examples of lower alkyl radicals for R, $R^1$ and substituents on the phenyl radical Ar are methyl, ethyl, n-propyl, iso-propyl, n-butyl and isobutyl. Examples of aryl radicals for $R^1$ are phenyl and substituted phenyl.

Lower alkoxy radicals include methoxy, ethoxy, propoxy and butoxy.

$R^1$ when heteroaryl can be indolyl e.g., 3-indolyl, thienyl, e.g., 2-thienyl, furyl, e.g., 2-furyl, and pyridyl e.g., 2- and 3-pyridyl.

Substituted phenyl radicals which can be used for $R^1$ or as the aryl portion of $R^1$ include phenyl substituted by one or more substituents chosen from halogen such as chlorine, fluorine, or bromine, alkoxy such as methoxy or ethoxy, alkyl such as methyl or ethyl, alkylenedioxy such as methylenedioxy, and ethylenedioxy, nitro, amino, akylamino, dialkylamino, acylamino, e.g., alkanoyl amino, hydroxy, lower-alkoxycarbonyl, trihalo lower alkyl e.g., trifluoromethyl, mercapto, methylthio, methanesulphonyl, alkylsulphonamido, e.g., methane sulphonamido, phenyl and phenyl substituted by any of the substituents mentioned in connection with the substituted phenyl radical.

The aralkyl radical $R^1$ includes benzyl and substituted benzyl.

The aroyl radical $R^1$ is preferably benzoyl or substituted benzoyl, such as halobenzoyl, e.g., p-chlorobenzoyl, lower alkylbenzoyl, e.g., p-methylbenzoyl or lower alkoxybenzoyl, e.g., p-methoxybenzoyl.

Cycloalkyl radicals for $R^1$ are cyclopentyl, cyclohexyl and cycloheptyl.

Preferably the —NRCXNHR$^1$ substituent in the compounds of formula I is in the 4-position.

The acid addition salts of the compound of formula I which are within the scope of the invention includes those formed from inorganic and organic acids in particular pharmaceutically acceptable acid addition salts such as the sulphate, hydrochloride, hydrobromide, hydroiodide, nitrate, phosphate, sulphonate, (such as the methane sulphonate and p-toluene sulphonate), acetate, maleate, fumarate, tartrate and formate salts.

The quaternary ammonium salts include those formed with alkyl halides (e.g., methyl bromide or chloride) and aralkyl halides (e.g., benzyl bromide or chloride).

The compounds of formula I exhibit pharmacological activity such as action on the cardiovascular system, especially hypotensive activity, when tested on warm blooded animals.

Compounds of formula I were tested for hypotensive activity by administering the compounds intravenously to normotensive rats.

Representative of the hypotensive activity of the compounds of this invention are 1-phenyl-3-[1-(4-phenyl-4-oxobutyl)piperid-4-yl]thiourea hydrochloride and 1-benzoyl-3-[1-(4-phenyl-4-oxobutyl)piperid-4-yl]urea hydrochloride which both showed good activity.

The preferred hypotensive agents of this invention are compounds having the formula:

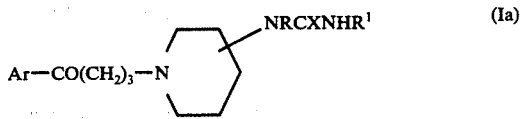   (Ia)

in which
R is hydrogen or lower alkyl;
$R^1$ is hydrogen, cyclohexyl, phenyl, benzoyl and substituted phenyl containing one or two substituents in which said substituent is halo, lower alkyl, lower alkoxy or trihalo(lower)alkyl;
X is oxygen or sulfur; Ar is phenyl; and
pharmaceutically acceptable acid addition salts thereof.

In addition some of the compounds of formula I have been found to manifest hypotensive activity when administered to hypertensive rats. This particular form of hypotensive activity is termed anti-hypertensive activity.

The test procedure for anti-hypertensive activity was to administer the compound under test orally to hypertensive rate whilst measuring the systolic pressure. In such a test 1-phenyl-3-[1-(4-phenyl-4-oxobutyl)-piperid-4-yl]urea hydrochloride showed marked antihypertensive activity at a dose of 40 mpk.

In addition certain compounds of formula I may be used as intermediates for other compounds of formula I.

The compounds of formula I may be prepared in a number of ways by building up the molecule from suitable starting materials in known manner. Such processes applied to the preparation of the novel compounds of formula I are included within the scope of the invention.

The preferred method for preparing compounds of formula I comprises reacting a compound of formula II

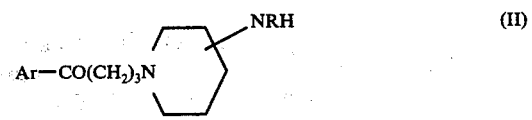   (II)

(wherein R and Ar are as defined in connection with formula I) with a compound of formula III

  (III)

wherein R¹ is as defined in connection with formula I except hydrogen and X is oxygen or sulphur. This reaction should be conducted under mild conditions to avoid the possibility of reaction between the amine II (when R is hydrogen) and the oxobutylene radical of another molecule of amine II giving a Schiffs base. Usually the reaction to form the compound of formula I takes place at room temperature.

The starting materials of formula II wherein R is hydrogen may be prepared by methods described in our British specification No. 1,345,872 (applications Nos. 42090/70 and 34376/71). The starting materials of formula II wherein R is lower alkyl may be prepared by alkylating corresponding compounds of formula II wherein R is hydrogen, or by methods analogous to those described in specification No. 1,345,872.

Compounds of formula I wherein R¹ is hydrogen may be prepared by hydrolysis of the corresponding compounds of formula I wherein R¹ is aroyl.

A second method for preparing compounds of formula I comprises reacting a compound of formula IV

  (IV)

wherein Ar is as defined in connection with formula I, and Y is a halogen atom or an equivalent replaceable atom or radical for example an organic sulphonyl radical such as a tosyl radical with a compound of formula V

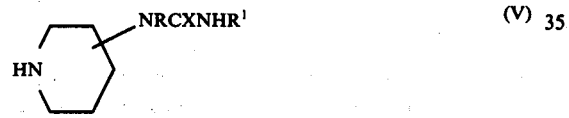  (V)

wherein R, R¹ and X are as defined in connection with formula I.

Compounds of formula IV may be prepared as described in British specification No. 1,345,872. Compounds of formula (V) may be prepared by known methods.

Once a compound of general formula I has been prepared then if necessary one or more substituents in the molecule may be converted to another substituent each within its own meanings specified in connection with formula I. For example compounds of formula I wherein R¹ represents hydrogen may be aroylated, for example using an active derivative of an acid of formula R¹COOH wherein R¹ is aryl, to give compounds of formula I wherein R¹ is aroyl. As examples of reactive derivatives of the acid of formula R¹COOH mention is made of the halide. e.g., the chloride and the anhydride.

When compounds of formula I are produced wherein Ar contains lower alkoxy or aryl lower alkoxy substituents hydrolysis or dealkylation to the corresponding hydroxy compounds may be brought about in known manner.

If necessary, in any of the reactions hereinbefore described, reactive substituent groups may be blocked during a reaction and released at a later stage.

A further method for preparing compounds of formula I wherein R is hydrogen which comprises reacting a compound of formula VI

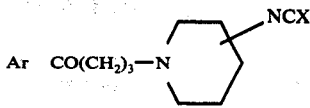

with an amine of formula:

$R^1NH_2$  (VII)

wherein Ar and X are as defined in connection with formula I and R¹ is as defined in connection with formula I except hydrogen or aroyl. This reaction should be conducted under mild conditions to avoid any possibility of the amine (VII) reacting with the oxobutylene group to form a Schiffs base.

Compounds of formula VI wherein Ar does not contain a hydroxy group may be prepared by treatment of a compound of formula II, wherein R is H with phosgene or thiophosgene followed by treatment of the product with calcium oxide according to the following reaction scheme:

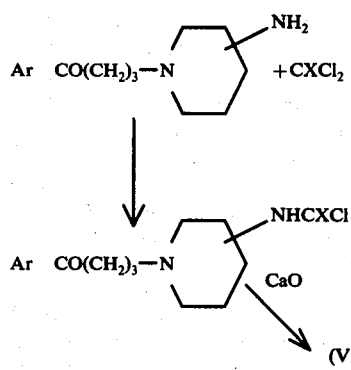

wherein Ar and X are as defined in connection with formula I. Other standard methods may be used to prepare compound (VI).

A method for preparing compounds of formula I wherein R¹ is hydrogen and X is oxygen comprises reacting a compound of formula II with nitrourea ($H_2NCONH.NO_2$)

The invention also includes pharmaceutical compositions containing as active ingredient an active compound of formula I as above defined. The active compound may be micronised if desired. In addition to the active ingredient, the compositions also contain a nontoxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilizers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following examples illustrate the invention.

EXAMPLE 1

1-Phenyl-3-[1-(4-phenyl-4-oxobutyl)piperid-4-yl]urea

To 4-Amino-1-(4-phenyl-4-oxobutyl)piperidine (1.23g) stirred at room temperature in benzene (125 ml) was added phenyl isocyanate (0.63 g., 5% excess) in benzene (25 ml). The product began to precipitate immediately. After stirring the reaction mixture for 18 hours, the title compound was filtered off as a white solid (1.55 g) which was dried and converted by treatment with ethanolic hydrogen chloride to the hydrochloride (1.57 g). (78%, m.p.> 190° C (dec) $C_{22}H_{27}N_3O_2$ HCl requires C 65.73; H 7.02; N 10.45% ; Found C 65.58; H 7.07; N 10.31%.

EXAMPLE 2

1-(4-Methoxyphenyl)-3-[1-(4-phenyl-4-oxobutyl)piperid-4-yl]urea.

4-Amino-1-(4-phenyl-4-oxobutyl)piperidine (1.23 g) and 4-methoxyphenyl isocyanate (0.82 g) were condensed together in benzene (125 ml) in the manner of Example 1 to give the title compound (1.3 g). Crystallization from EtOH/HCL afforded the hydrochloride (1.26 g), m.p. 199.2° C. $C_{23}H_{29}N_3O_3$ HCl requires C 63.89; H 6.94; N 9.72%; Found C 64.52; H 6.85; N 9.71%.

EXAMPLE 3

1-(3-Toluyl)-3-[1-(4-phenyl-4-oxobutyl)piperid-4-yl]urea.

4-Amino-1-(4-phenyl-4-oxobutyl)piperidine (1.23g) and 3-toluyl isocyanate (0.73 g) were condensed together in benzene (125 ml) in the manner of Example 1 to give the title compound (1.1 g). Crystallization from EtOH/HCl afforded the hydrochloride (0.7 g), m.p. 181.6° C $C_{23}H_{29}N_3O_2$ HCl requires C 63.60; H 7.37; N 9.68%; Found C 64.07; H 7.34; N 9.77%.

EXAMPLE 4

1-(2,6-Dimethylphenyl)-3-[1-(4-phenyl-4-oxobutyl)-piperid-4yl]urea.

4-Amino-1-(4-phenyl-4-oxobutyl)piperidine (1.23 g) and 2,6-dimethylphenyl isocyanate (0.81 g) were condensed together in benzene (125 ml) in the manner of Example 1 to give the title compound (1.1. g). Crystallization from EtOH/HCl afforded the hydrochloride (0.85 g) m.p. 214.2° C.

$C_{24}H_{31}N_3O_2$ HCl requires C 67.06; H 7.45; N 9.78%; Found C 67.44; H 7.55; N 9.54%.

EXAMPLE 5

1-(2-Trifluoromethylphenyl)-3-[1-(4-phenyl-4-oxobutyl)piperid-4-yl]urea.

4-Amino-1-(4-phenyl-4-oxobutyl)piperidine (1.23 g) and 2-trifluoromethylphenyl isocyanate (1.03 g) were condensed together in benzene (125 ml) in the manner of Example 1 to give the title compound (1.01 g). Crystallization from EtOH/HCl afforded the hydrochloride (0.67 g), m.p. 193.7° C $C_{23}H_{26}F_3N_3O_2$ HCl requires C 58.73; H 5.75; N 8.94%; Found C 58.88; H 5.93; N 8.79%.

EXAMPLE 6

1-(4-Chlorophenyl)-3-[1-(4-phenyl-4-oxobutyl)piperid-4-yl]urea

4-Amino-1-(4-phenyl-4-oxobutyl)piperidine (1.23 g) and 4-chlorophenyl isocyanate (0.85 g) were condensed together in benzene (125 ml) in the manner of Example 1 to give the title compound (1.5 g). Crystallization from EtOH/HCl afforded the hydrochloride (1.12 g), m.p. 245.0° C.

$C_{22}H_{26}ClN_3O_2$ HCl requires C 60.50; H 6.19; N 9.63% Found C 60.75; H 6.40; N 9.59 %.

EXAMPLE 7

1-(3,4-Dichlorophenyl)-3-[1(4-phenyl-4-oxobutyl)piperid-4-yl]urea

4-Amino-1-(4-phenyl-4-oxobutyl)piperidine (1.23 g) and 3,4-dichlorophenyl isocyanate (1.03 g) were condensed together in benzene (125 ml) in the manner of Example 1 to give the title compound (1.2g). Crystallization from EtOH/HCl afforded the hydrochloride (1.12 g), m.p. 217.9° C.

$C_{22}H_{25}Cl_2N_3O_2$ HCl requires C 56.07; H 5.52; N 8.82%; Found C 56.00; H 5.66; N 8.81%.

EXAMPLE 8

1-Phenyl-3-(1-[3-benzoylpropyl]piperid-4-yl)thiourea

4-Amino-1-(4-phenyl-4-oxobutyl)piperidine (1.23 g., 0.005 mole) in benzene (125 ml.) was treated with phenyl isothiocyanate (0.74 g., 0.0055 mole) and the mixture stirred at room temperature for 24 hours. The precipitated title compound was filtered off, washed with a little fresh benzene and dried (1.17 g.). Conversion to the hydrochloride was achieved by dissolving in ethanol, adding a solution of ethanol saturated with HCl until just acid then sufficient ether to promote crystallization. Filtration afforded the title compound hydrochloride as colorless needles (1.17 g.), m.p. 221.3°.

Analysis: Found: C, 62.87; H, 7.07; N, 9.94. $C_{22}H_{27}N_3OS.HCl$ requires: C, 63.21; H, 6.75; N, 10.05%.

EXAMPLE 9

1-Cyclohexyl-3-[1(4-phenyl-4-oxobutyl)piperid-4-yl]urea

4-Amino-1-(4-phenyl-4-oxobutyl)piperidine (1.23g, 0.005 mole) was dissolved in benzene (50 ml.) and the mixture treated with cyclohexyl isocyanate (0.685 g, 0.0055 mole). After stirring for 18 hours, the mixture was filtered to afford the title compound hemihydrate as colorless crystals, (0.952 g), m.p. 178.6°.

Analysis: Found: C, 69.20; H, 9.00; N, 10.79. $C_{22}H_{33}N_3O_2 \cdot \tfrac{1}{2}H_2O$ requires: C, 69.44; H, 9.01; N, 11.04%

EXAMPLE 10

1-(3-Trifluoromethylphenyl)-3-[1(4-phenyl-4-oxobutyl)piperid-4-yl]urea

4-Amino-1-(4-phenyl-4-oxobutyl)piperidine (1.232g) and 3-trifluoromethylphenyl isocyanate (1.03g, 5% excess) were condensed together in benzene (150 mls.) in the manner of Example 1 to give the title compound as a white solid (1.28g). Crystallization from ethanolic hydrogen chloride afforded the hydrochloride (1.006g, m.p. 192.5° C)

$C_{23}H_{26}F_3N_3O_2.HCl.H_2O$ requires: C 56.56; H 5.53; N 8.60 % found: C 56.60; H 5.79; N 8.53%.

EXAMPLE 11

1-Benzoyl-3-[1-(4-phenyl-4-oxobutyl)piperid-4-yl]urea

4-Amino-1-(4-phenyl-4-oxobutyl)piperidine (1.232g) was treated with benzoyl isocyanate (0.81 g, 5% excess) in the manner of Example 1. The title compound was obtained as a white solid by evaporation of the reaction mixture (1.81g). Crystallization from ethanolic hydrogen chloride afforded the hydrochloride (1.200 g, m.p. 201.6° C).

$C_{23}H_{27}N_3O_3.HCl.2H_2O$ requires: C 59.28; H 6.92; N 9.02%; found: C 59.43; H 6.97; N 8.84%.

EXAMPLE 12

1-Benzoyl-3-[1-(4-phenyl-4-oxobutyl)piperid-4-yl]thiourea

To ammonium isothiocyanate (0.42g) in dry acetone (7 mls) was added benzoyl chloride (0.71 g) and the mixture refluxed for 5 minutes. To this solution was added 4-amino-1-(4-phenyl-4-oxobutyl)piperidine (1.23 g) in dry acetone (10 mls) and the mixture refluxed 10 minutes. The solution was poured into water (100 mls) and the mixture extracted with chloroform. The title compound was obtained as a buff solid by evaporation of the chloroform extract. Crystallization from ethanolic hydrogen chloride afforded the hydrochloride (0.580g, m.p. 187.0° C).

$C_{23}H_{27}N_3O_2S.HCl.\tfrac{1}{4}H_2O$ requires: C 61.27; H 6.33; N 9.32%; Found: C 61.17; H 6.64; N 9.17%.

EXAMPLE 13

3-[1-(4-Phenyl-4-oxobutyl)piperid-4-yl]urea

1-Benzoyl-3-[1-(4-phenyl-4-oxobutyl)piperid-4-yl]urea, prepared according to Example 11, may be hydrolyzed to give the title compound.

EXAMPLES 14(a) – (p)

Repeating the procedure of Example 1, the following ureas of formula I may be prepared according to the reaction:

$$Ar-CO(CH_2)_3N\underset{(II)}{\bigcirc}-NRH + R^1NCX \longrightarrow$$

$$ArCO(CH_2)_3N\underset{(I)}{\bigcirc}-NRCXNHR^1$$

wherein A, R, $R^1$ and X are as defined below:

| | Ar | R | $R^1$ | X |
|---|---|---|---|---|
| (a) | p-hydroxyphenyl | H | phenyl | O |
| (b) | p-methoxyphenyl | H | phenyl | O |
| (c) | p-fluorophenyl | H | phenyl | O |
| (d) | phenyl | methyl | phenyl | O |
| (e) | 2,5-dimethylphenyl | H | phenyl | O |
| (f) | p-chlorophenyl | H | phenyl | S |
| (g) | p-benzyloxyphenyl | H | phenyl | S |
| (h) | m-trifluoromethylphenyl | H | phenyl | S |
| (i) | phenyl | H | 2-thienyl | O |
| (j) | phenyl | H | 2-furyl | O |
| (k) | phenyl | H | 2-pyridyl | O |
| (l) | phenyl | H | methyl | O |
| (m) | phenyl | H | benzyl | O |
| (n) | phenyl | H | p-chlorobenzoyl | O |
| (o) | phenyl | H | p-methylbenzoyl | O |
| (p) | phenyl | H | p-methoxybenzoyl | O |

EXAMPLE 15

1-Phenyl-3-[1-(4-phenyl-4-oxobutyl)piperid-3-yl]urea

By a procedure analogous to Example 1, 3-amino-1-(4-phenyl-4-oxobutyl)piperidine may be reacted with phenyl isocyanate to give the title compound.

EXAMPLE 16

1-Benzoyl-3-[1-(4-phenyl-4-oxobutyl)piperid-4-yl]urea

3-[1-(4-Phenyl-4-oxobutyl)piperid -4-yl]urea may be reacted with benzoyl chloride in the presence of dry benzene solvent and anhydrous pyridine to give the title compound, the hydrochloride dihydrate salt of which has a melting point of 201.6° C.

We claim:

1. A compound of the formula:

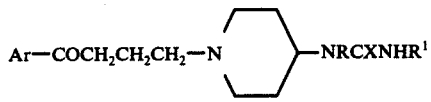

in which
R is hydrogen or lower alkyl;
R¹ is hydrogen, lower alkyl, cyclohexyl, benzyl, phenyl, benzoyl, substituted phenyl wherein the substituent is at least one member selected from the group consisting of halo, lower alkyl, lower alkoxy and trihalo(lower)alkyl, or substituted benzoyl wherein the substituent is at least one member selected from the group consisting of halo, lower alkyl and lower alkoxy;
Ar is phenyl or substituted phenyl wherein the substituent is at least one member selected from the group consisting of halo, lower alkoxy, benzyloxy, hydroxy, lower alkyl and triflouromethyl);
X is oxygen or sulphur;
or a pharmaceutically acceptable acid addition or quaternary ammonium salt thereof.

2. A compound of claim 1 having the formula:

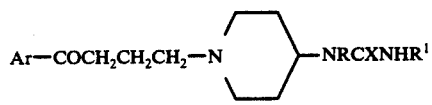

in which
R is hydrogen or lower alkyl;
R¹ is hydrogen, cyclohexyl, phenyl, benzoyl or substituted phenyl containing one or two substituents selected from the group consisting of halo, lower alkyl, lower alkoxy and trihalo(lower) alkyl;
X is oxygen or sulfur;
Ar is phenyl;
or a pharmaceutically acceptable acid addition salt thereof.

3. A compound of the formula:

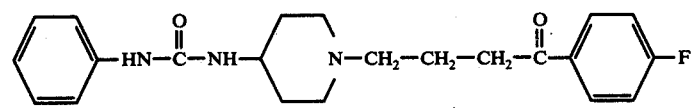

or a pharmaceutically acceptable acid addition or quaternary ammonium salt thereof.

4. A compound as claimed in claim 1 which is 1-phenyl-3-[1-(4-phenyl-4-oxobutyl)piperid-4-yl]urea or a pharmaceutically acceptable acid addition or quaternary ammonium salt thereof.

5. A compound as claimed in claim 1 which is 1-(4-methoxyphenyl)-3-[1-(4-phenyl-4-oxobutyl)piperid-4yl]urea or a pharmaceutically acceptable acid addition or quaternary ammonium salt thereof.

6. A compound as claimed in claim 1 which is 1-(3-toluyl)-3-[1-(4-phenyl-4-oxobutyl)piperid-4-yl]urea or a pharmaceutically acceptable acid addition or quaternary ammonium salt thereof.

7. A compound as claimed in claim 1 which is 1-(2,6-dimethylphenyl)-3-[1-(4-phenyl-4-oxobutyl)-piperid-4-yl]urea or a pharmaceutically acceptable acid addition or quaternary ammonium salt thereof.

8. A compound as claimed in claim 1 which is 1-(2-trifluoromethylphenyl)-3-[1-(4-phenyl-4-oxobutyl)-piperid-4-yl]urea or a pharmaceutically acceptable acid addition or quaternary ammonium salt thereof.

9. A compound as claimed in claim 1 which is 1-(4-chlorophenyl)-3-[1-(4-phenyl-4-oxobutyl)piperid-4-yl]urea or a pharmaceutically acceptable acid addition or quaternary ammonium salt thereof.

10. A compound as claimed in claim 1 which is 1-(3,4-dichlorophenyl)-3-[1-(4-phenyl-4-oxobutyl)piperid-4-yl]urea or a pharmaceutically acceptable acid addition or quaternary ammonium salt thereof.

11. A compound as claimed in claim 1 which is 1-phenyl-3-(1-[3-benzoylpropyl]piperid-4-yl)thiourea or a pharmaceutically acceptable acid addition or quaternary ammonium salt thereof.

12. A compound as claimed in claim 1 which is 1-cyclohexyl-3-[1-(4-phenyl-4-oxobutyl)piperid-4-yl]urea or a pharmaceutically acceptable acid addition or quaternary ammonium salt thereof.

13. A compound as claimed in claim 1 which is 1-(3-trifluoromethylphenyl)-3-[1-(4-phenyl-4-oxobutyl)-piperid-4-yl]urea or a pharmaceutically acceptable acid addition or quaternary ammonium salt thereof.

14. A compound as claimed in claim 1 which is 1-benzoyl-3-[1-(4-phenyl-4-oxobutyl)piperid-4-yl]urea or a pharmaceutically acceptable acid addition or quaternary ammonium salt thereof.

15. A compound as claimed in claim 1 which is 1-benzoyl-3-[1-(4-phenyl-4-oxobutyl)piperid-4-yl]thiourea or a pharmaceutically acceptable acid addition or quaternary ammonium salt thereof.

* * * * *